(12) United States Patent
Yasui et al.

(10) Patent No.: US 7,355,694 B2
(45) Date of Patent: Apr. 8, 2008

(54) METHOD AND APPARATUS FOR MEASURING A PARTICLE DIAMETER OF FOAM ON A MALT ALCOHOLIC DRINK

(75) Inventors: Kazuhisa Yasui, Yaizu (JP); Toshio Kurihara, Yaizu (JP); Masachika Takashio, Yaizu (JP)

(73) Assignee: Sapporo Breweries Limited, Tokyo (JP)

( * ) Notice: Subject to any disclaimer, the term of this patent is extended or adjusted under 35 U.S.C. 154(b) by 164 days.

(21) Appl. No.: 10/524,696

(22) PCT Filed: Sep. 10, 2003

(86) PCT No.: PCT/JP03/11574

§ 371 (c)(1),
(2), (4) Date: Feb. 15, 2005

(87) PCT Pub. No.: WO2004/025220

PCT Pub. Date: Mar. 25, 2004

(65) Prior Publication Data

US 2006/0119847 A1 Jun. 8, 2006

(30) Foreign Application Priority Data

Sep. 10, 2002 (JP) .............................. 2002-263661

(51) Int. Cl.
*G01N 21/90* (2006.01)
(52) U.S. Cl. .............................. 356/239.5; 356/239.4; 356/239.6; 356/239.8
(58) Field of Classification Search ........ 356/335–343, 356/239.4, 239.6, 240.1, 426–428; 250/223 B, 250/498.1, 208.1; 382/141–142; 73/60.11
See application file for complete search history.

(56) References Cited

U.S. PATENT DOCUMENTS

| 3,232,429 A | * | 2/1966 | Norwich ..................... 209/524 |
| 5,510,620 A | * | 4/1996 | Achter et al. .......... 250/339.12 |
| 5,536,935 A | | 7/1996 | Klotzsch et al. |
| 5,542,004 A | * | 7/1996 | Constant et al. ............ 382/141 |
| 6,025,909 A | * | 2/2000 | Juvinall et al. .......... 356/239.4 |
| 6,226,081 B1 | * | 5/2001 | Fantone et al. .......... 356/239.6 |
| 6,275,603 B1 | * | 8/2001 | Cronshaw et al. .......... 382/142 |
| 6,439,035 B1 | * | 8/2002 | Yasui et al. ................. 73/60.11 |

FOREIGN PATENT DOCUMENTS

| EP | 655610 | | 5/1995 |
| JP | 4-50711 | | 2/1992 |
| JP | 04142290 A | * | 5/1992 |
| JP | 10-176908 | | 6/1998 |
| JP | 2000180358 A | * | 6/2000 |
| WO | 99/30149 | | 6/1999 |
| WO | 00/42381 | | 7/2000 |

* cited by examiner

*Primary Examiner*—Sang H. Nguyen
(74) *Attorney, Agent, or Firm*—Oblon, Spivak, McClelland, Maier & Neustadt, P.C.

(57) ABSTRACT

A method and apparatus for measuring the particle diameter of foam on a malt alcoholic drink, which can detennine the quality of the foam of the malt alcoholic drink objectively, are provided. The apparatus for measuring the particle diameter of foam on a malt alcoholic drink according to the present invention includes a laser light source for irradiating a linear laser beam onto the surface of a foam layer created on a malt alcoholic drink, an imaging device for imaging a laser line reflected on the surface of the foam layer to obtain an image of the laser line, and a calculating device for obtaining edge information of the laser line from the image of the laser line to calculate the particle diameter of foam in the foam layer based on the edge information.

5 Claims, 4 Drawing Sheets

SIDE VIEW

TOP VIEW

FIG.4A    FIG.4B    FIG.4C
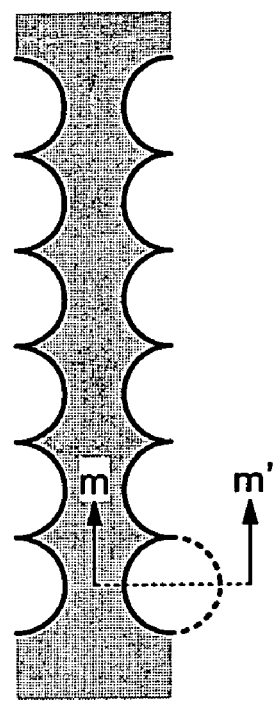
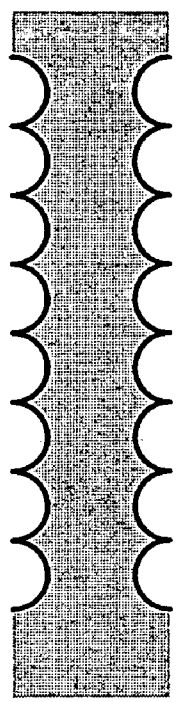
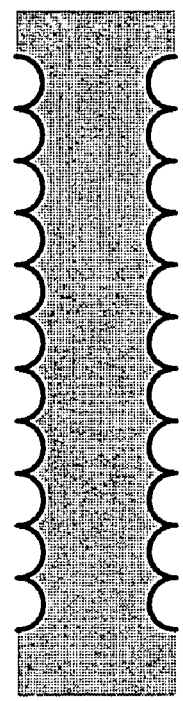
FIG.4D
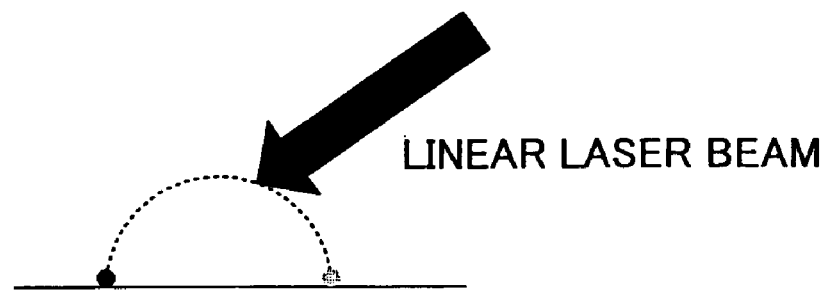
LINEAR LASER BEAM

METHOD AND APPARATUS FOR MEASURING A PARTICLE DIAMETER OF FOAM ON A MALT ALCOHOLIC DRINK

TECHNICAL FIELD

The present invention relates to a method for measuring a particle diameter of foam on a malt alcoholic drink and an apparatus for measuring the particle diameter of foam on a malt alcoholic drink.

BACKGROUND ART

As a malt alcoholic drink such as beer and low-malt beer is poured into a vessel at the time of drinking, a foam layer is created on the surface of the malt alcoholic drink. The property of the foam layer is one important factor indicating the quality of the malt alcoholic drink.

The property of the foam layer is represented by the degree of foaming, the thickness of the foam layer, the continuity of the foam layer (foam retention), the size of the particle diameters of foam, and the adhesive property of foam to the vessel, etc., and is a parameter for evaluating each foam layer objectively.

With respect to the particle diameter of foam, a foam layer composed of fine and uniform foam particles is called as creamy, continuous, and high quality foam to the eye. On the other hand, large and coarse foam particles that are created immediately after pouring into a vessel and collapse rapidly on the upper layer in a foam layer have no continuity. When such large and coarse foam particles are relatively abundant, the overall continuity of the foam layer is small and it is not a creamy foam. Accordingly, the property of created foams can be determined by measuring the particle diameter of the foam. The measure of the particle diameter of foam not only determines the property of foam on a malt alcoholic drink such as beer and low-malt beer, but also can be applied to determine whether or not very fine and creamy foam particles have been created, for example, in a foam layer of whipped cream.

However, no measuring method capable of appropriately measuring the particle diameter of foam on malt alcoholic drinks has been established and the measure of the particle diameter of foam has to depend on visual evaluation in the present circumstances, so that it is difficult to obtain an accurate measurement of the particle diameter of foam.

DISCLOSURE OF THE INVENTION

One of the objects of the present invention is to provide a method for measuring a particle diameter of foam on a malt alcoholic drink, which can determine the quality of the foam of the malt alcoholic drink objectively.

Another object of the present invention is to provide an apparatus for measuring a particle diameter of foam on a malt alcoholic drink, which can determine the quality of the foam of the malt alcoholic drink objectively.

One of the objects can be achieved by a method for measuring a particle diameter of foam on a malt alcoholic drink, which includes the steps of irradiating a linear laser beam onto a surface of a foam layer created on a malt alcoholic drink, imaging a laser line reflected on the surface of the foam layer by an imaging device to obtain an image of the laser line, and obtaining edge information of the laser line from the image of the laser line to calculate a particle diameter of foam in the foam layer based on the edge information.

In the method for measuring a particle diameter of foam on a malt alcoholic drink, preferably, the linear laser beam is obliquely irradiated onto the surface of the foam layer and the laser line is imaged from a position in a direction perpendicular to the surface of the foam layer.

Also, one of the objects can be achieved by an apparatus for measuring a particle diameter of foam on a malt alcoholic drink, which includes a laser light source that irradiates a linear laser beam onto a surface of a foam layer created on a malt alcoholic drink, an imaging device that images a laser line reflected on the surface of the foam layer to obtain an image of the laser line, and a calculating device that obtains edge information of the laser line from the image of the laser line to calculate a particle diameter of foam in the foam layer based on the edge information.

Other objects and features of the present invention will become more apparent from the following detailed description illustrated in conjunction with the accompanying drawings.

BRIEF DESCRIPTION OF THE DRAWINGS

FIGS. 4A-4D are diagrams showing concavity and convexity observed on edge portions of a laser line.

BEST MODE FOR CARRYING OUT THE INVENTION

The embodiments of the present invention are illustrated in detail in conjunction with drawings bellow.

Figure 1:
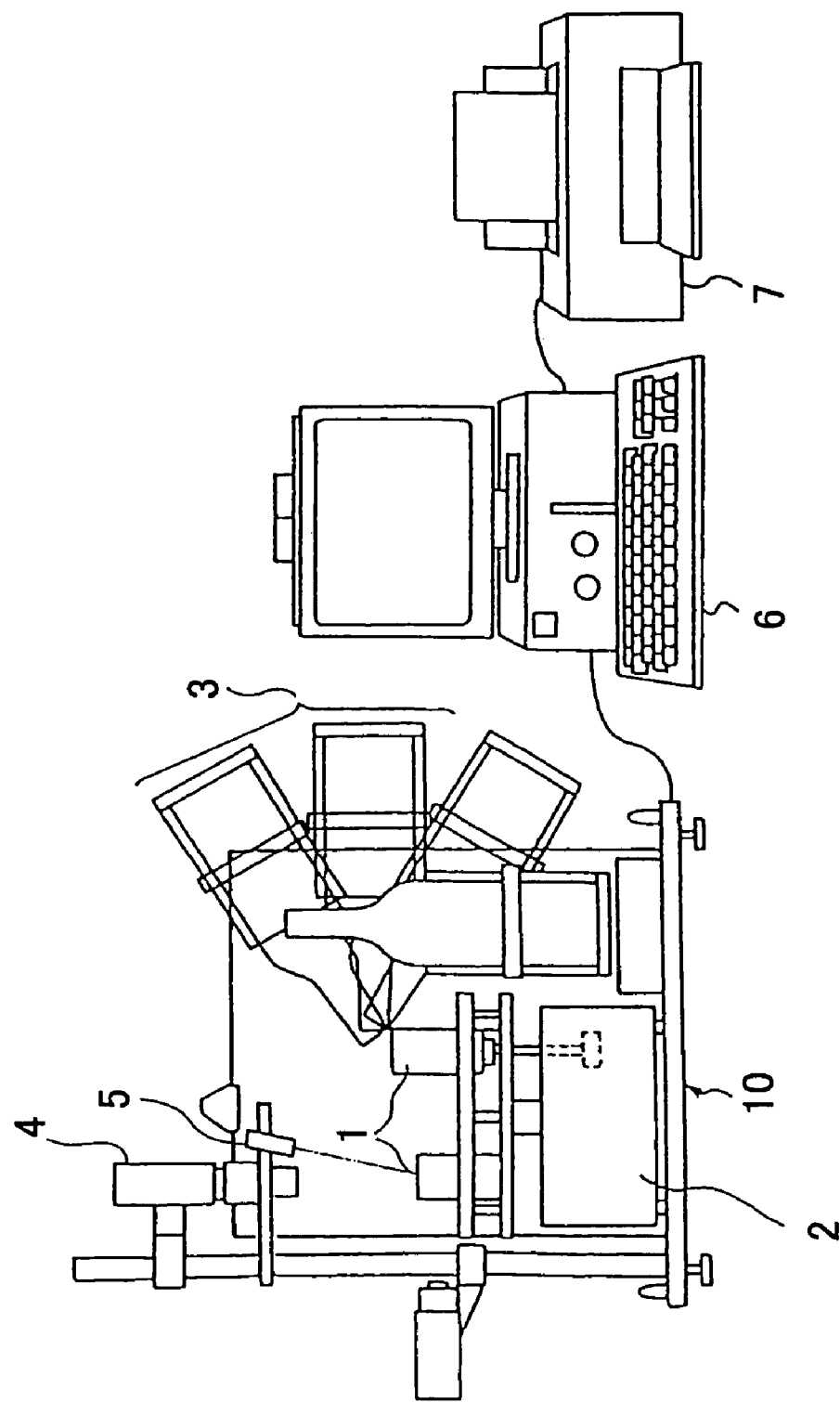
FIG. 1 is a diagram showing an apparatus for measuring the particle diameter of foam on a malt alcoholic drink according to the present invention.

First, an apparatus for measuring the particle diameter of foam on a malt alcoholic drink according to the present invention is illustrated using FIG. 1. The apparatus for measuring the particle diameter of foam on a malt alcoholic drink according to the present invention is also an apparatus for determining the quality of foam on a malt alcoholic drink and, for simplicity, is referred to as a foam quality-evaluating apparatus below. Also, an example of beer employed as the malt alcoholic drink is illustrated.

A foam quality-evaluating apparatus shown in FIG. 1 is composed of a beer-pouring-out device 10, a data processing device 6, and a data output device 7. Herein, the beer-pouring-out device 10 includes a turntable 2, a beer-pouring-out mechanism 3, a CCD camera 4, and a linear laser light source 5. Also, the turntable 2 supports a vessel such as a test glass 1 and can move the test glass 1 to a position at which beer is poured out and a position at which foam on beer can be imaged. Further, the beer-pouring-out mechanism 3 holds a beer bottle and pours out beer into the test glass 1. An imaging device such as the CCD camera 4 images foam created on the surface of beer from above. Additionally, the linear laser light source 5 irradiates a linear laser beam into the test glass 1. The laser light source 5 is composed of, for example, an aspheric lens and a rod lens. As a laser light source for emitting such a linear laser beam, for example, LM10 produced by FM Laser Tec. Co., Ltd. can be used. A linear laser beam with a line width equal to or less than 1 mm can be obtained by using the laser light source.

Also, the foam quality-evaluating apparatus shown in FIG. 1 includes a personal computer 6 with a monitor and a printer 7. Herein, the personal computer 6 with a monitor sets and controls the operation of the beer-pouring-out device 10 and processes obtained measurement data, and the printer 7 prints out the measurement data.

Figure 2:
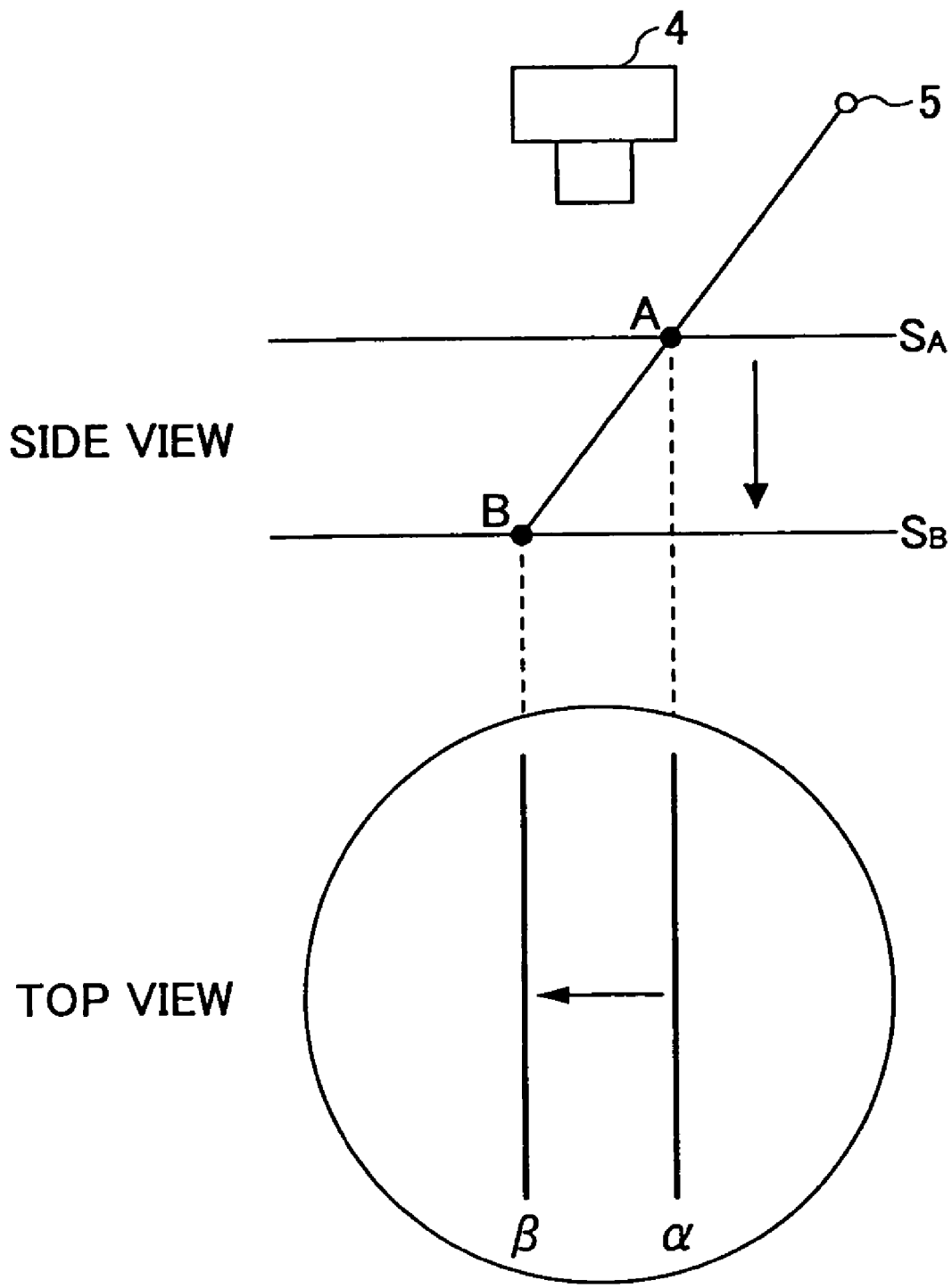
FIG. 2 is a diagram illustrating the principle of a method for measuring the particle diameter of foam on a malt alcoholic drink according to the present invention.

Next, the principle of a method for measuring the particle diameter of foam on beer being a malt alcoholic drink according to the present invention is illustrated using FIG. 2. First, in the foam quality-evaluating apparatus, beer is poured into the test glass 1 from the beer-pouring-out mechanism 3 and the turntable 2 is rotated so that the test glass 1 is moved to a position at which foam on the beer can be imaged. At this time, a foam layer has been created on the surface of the beer poured into the test glass 1. Then, a linear laser beam is irradiated from the laser light source 5 to the beer poured into the test glass 1 and the beer poured into the test glass 1 is imaged from above the test glass 1 using the CCD camera 4. For more detail, the linear laser beam is obliquely irradiated on the surface of the foam layer created on the beer poured into the test glass 1 from the laser light source 5 located obliquely upward relative to the test glass 1 and a laser line is reflected on the surface of the foam layer. The laser line reflected on the surface of the foam layer is imaged by the CCD camera 4.

As shown in the upper part of FIG. 2, as the beer poured into the test glass 1 is observed from the side over time, the foam layer created on the surface of the beer poured into the test glass 1 collapses over time, so that the surface of the foam layer (foam surface) falls from an initial foam surface $S_A$ to a foam surface $S_B$. At this time, the laser line reflected on the surface of the foam layer moves from position A to position B.

Also, as shown in the lower part of FIG. 2, as the beer poured into the test glass 1 is observed from the top surface over time, the laser line reflected on the surface of the foam layer moves from position $\alpha$ to position $\beta$ while the height of the foam surface falls from the height of the foam surface $S_A$ to the height of the foam surface $S_B$. That is, when the foam surface is at the height of $S_A$, the laser line is at the position of $\alpha$, and when the foam surface is at the height of $S_B$, the laser line is at the position of $\beta$.

Figure 3:
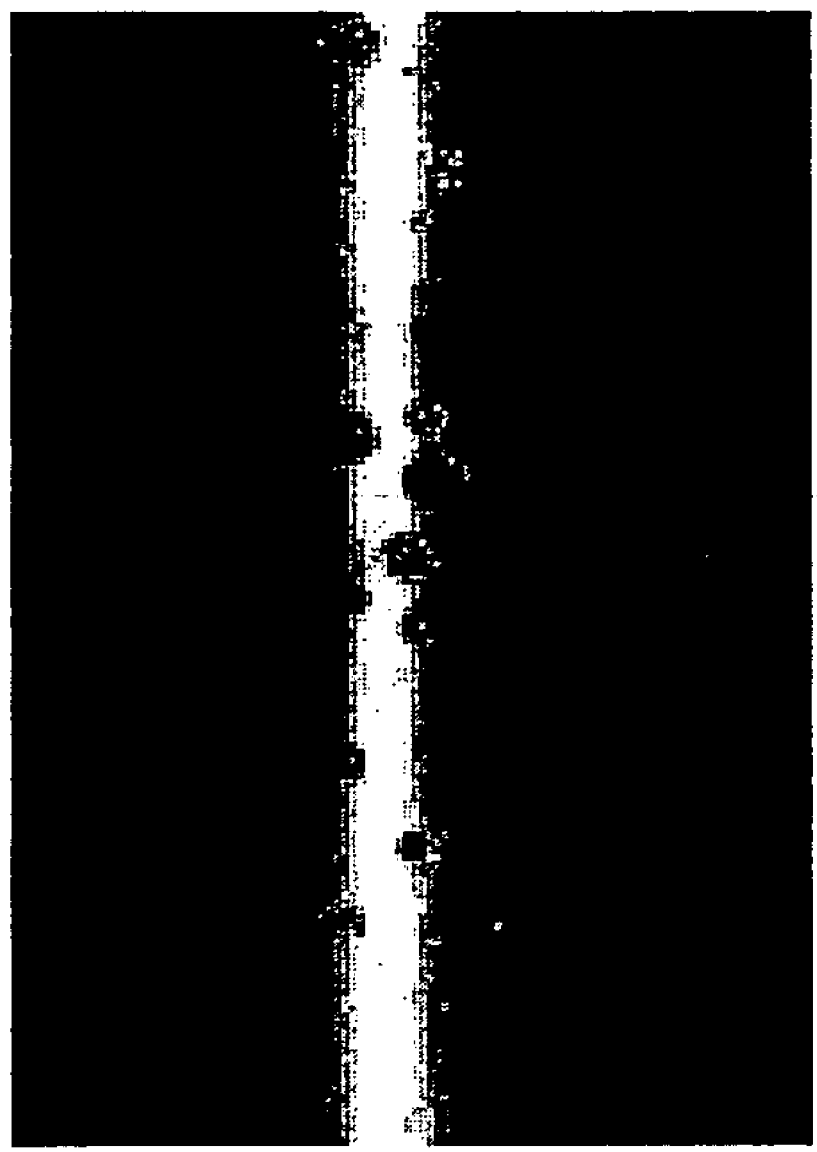
FIG. 3 is a drawing that illustrates one example of a laser line image obtained by imaging the laser line reflected on the surface of a foam layer by a CCD camera.

FIG. 3 shows one example of a laser line image obtained by imaging a laser line reflected on the surface of a foam layer by a CCD camera. As shown in FIG. 3, a linear laser beam is emitted from the laser light source 5 and a whitely shining linear laser line with a width of approximately 1 mm is reflected on the surface of the foam layer on the beer. Concavity and convexity formed by foam particles are observed on edge portions of the laser line.

FIGS. 4A-4D are schematic diagrams for illustrating a laser line reflected on the surface of a foam layer on beer in detail, which show concavity and convexity observed on edge portions of the laser line. Herein, it is assumed that foam particles having equal particle diameters are aligned along both edge portions of a laser line reflected on the surface of a foam layer on beer. FIG. 4A shows the alignment of foam particles having relatively large particle diameters, FIG. 4C shows the alignment of foam particles having relatively small particle diameters, and FIG. 4B shows the alignment of foam particles having intermediate particle diameters. Additionally, FIG. 4D is a cross-sectional view along the m-m' directions of one of foam particles present on edge portions of the laser line shown in FIG. 4A. That is, when the linear laser beam from the laser light source 5 is obliquely irradiated onto the surface of the foam layer on the beer as shown in FIG. 4D, the concavity and convexity are formed on the edge portions of the laser line by the foam particles aligned on the surface of the foam layer on the beer in FIGS. 4A-4C. Such laser line having concavity and convexity on the edge portions is imaged by the CCD camera 4. Then, an obtained laser line image as shown in FIG. 3 is image-processed by the personal computer 6 with a monitor so as to define the concavity and convexity on the edge portions of the laser line.

As the brightness of the laser line image is detected as image processing for the laser line image by the personal computer 6 with a monitor, the profiles of foam particles present on edge portions of the laser line image can be observed. That is, bright portions in the laser line image indicate the linear laser beam and dark portions on the edge portions of the laser line image indicate the foam particles. Herein, the particle diameter of the foam can be calculated by evaluating the size of the dark portion on the edge portions of the laser line image. For example, a signal of the image with respect to the edge portions of the laser line is binarized while a certain threshold value of the brightness is set, so as to distinguish the bright portions from the dark portions on the edge portions of the laser line. At this time, the definite profiles of the concavity and convexity caused by the foam particles on the edge portions of the laser line can be detected by selecting the threshold value of the brightness appropriately, as shown in FIGS. 4A, 4B, and 4C. Since a two-dimensional waveform with respect to the brightness of the obtained laser line image reflects how large the particle diameter of foam is, various techniques for measuring and analyzing the waveform can be applied in order to digitize the particle diameter of foam. For example, a reference gage is prepared in an image processing software and the amplitudes of the two-dimensional waveform are each measured by the gage, so as to determine the diameter of the individual foam particles directly.

Also, the profiles of the concavity and convexity on the edge portions of the laser line are perceived as the collection of picture elements on an image-processing screen. In an obtained image from above the glass, the respective picture elements that form the profile correspond to the information of the height viewed from the side as shown in FIG. 2, which can be obtained through digitization. The dispersion of the information of the heights of all picture elements that form the profile reflects the size of the foam particle that causes the formation of the concavity and convexity and the sizes of the foam particles can be compared by the comparison of statistics (e.g. deviations or dispersions) as the dispersion degrees of the height information. The image processing for the laser line image and the evaluation of the particle diameter of the foam are performed in a processing unit of the personal computer 6 with a monitor in the foam quality-evaluating apparatus shown in FIG. 1.

As described above, in the foam quality-evaluating apparatus as shown in FIG. 1, beer is poured into the test glass 1 using the beer-pouring-out apparatus 10, a linear laser beam from the laser light source 5 is irradiated onto a foam layer created on the beer, a laser line reflected on the surface of the foam layer is imaged by the CCD camera 4, an obtained laser line image is image-processed by the personal computer 6 with a monitor so as to obtain information for the profile of edge portions of the laser line (edge information), and the particle diameter of foam in the foam layer created on the beer can be determined based on the information of the profile. Additionally, as shown in FIG. 2, the degree of foam retention of beer can be also determined by observing a foam layer created on the beer using the foam quality-evaluating apparatus as shown in FIG. 1, immediately after pouring the beer into the test glass 1 and after a predetermined time has passed since the beer is poured. Also, the number of concavities and convexities on edge portions of a laser line, that is, the number of foam particles on the edge portions of the laser line can be digitized and the size of the foam particles can be also digitized by obtaining information for the profile of the edge portions of the laser line as described above.

Although the preferred embodiments of the present invention are described above in detail, the present invention is not limited to the above-mentioned embodiments and the embodiments can be improved and modified within the scope of the claims.

INDUSTRIAL APPLICABILITY

As described above, the particle diameter of foam on a malt alcoholic drink can be measured to determine the quality of the foam on the malt alcoholic drink objectively, using a method for measuring the particle diameter of foam on a malt alcoholic drink and an apparatus for measuring the particle diameter of foam on a malt alcoholic drink, according to the present invention.

The invention claimed is:

1. A method for measuring a particle diameter of foam on a malt alcoholic drink, characterized by comprising the steps of:
   irradiating a linear laser beam onto a surface of a foam layer created on a malt alcoholic drink;
   imaging a laser line reflected on the surface of the foam layer by an imaging device to obtain an image of the laser line; and
   obtaining edge information of the laser line from the image of the laser line to display a particle diameter of foam in the foam layer based on the edge information.

2. The method for measuring a particle diameter of foam on a malt alcoholic drink as claimed in claim 1, wherein
   the linear laser beam is obliquely irradiated onto the surface of the foam layer, and
   the laser line is imaged from a position in a direction perpendicular to the surface of the foam layer.

3. The method for measuring a particle diameter of foam on a malt alcoholic drink as claimed in claim 1, wherein said edge information comprises information which determines a concavity and convexity of foam particles on edge portions of said laser line so as to allow the particle diameter of the foam particles to be determined.

4. An apparatus for measuring a particle diameter of foam on a malt alcoholic drink, which comprises:
   a laser light source that irradiates a linear laser beam onto a surface of a foam layer created on a malt alcoholic drink;
   an imaging device that images a laser line reflected on the surface of the foam layer to obtain an image of the laser line; and
   a calculating device that obtains edge information of the laser line from the image of the laser line to calculate a particle diameter of foam in the foam layer based on the edge information.

5. The apparatus for measuring a particle diameter of foam on a malt alcoholic drink as claimed in claim 4, wherein said edge information comprises information which determines a concavity and convexity of foam particles on edge portions of said laser line so as to allow the particle diameter of the foam particles to be determined.

* * * * *